United States Patent
Huang et al.

(10) Patent No.: US 12,121,611 B2
(45) Date of Patent: Oct. 22, 2024

(54) ORAL CARE COMPOSITION, AND PREPARATION METHOD AND APPLICATION THEREOF

(71) Applicant: WUHAN UNIVERSITY, Hubei (CN)

(72) Inventors: Cui Huang, Hubei (CN); Yue Xu, Hubei (CN); Jingmei Guo, Hubei (CN)

(73) Assignee: WUHAN UNIVERSITY, Hubei (CN)

( * ) Notice: Subject to any disclaimer, the term of this patent is extended or adjusted under 35 U.S.C. 154(b) by 0 days.

(21) Appl. No.: 18/571,259

(22) PCT Filed: Nov. 15, 2022

(86) PCT No.: PCT/CN2022/131838
§ 371 (c)(1),
(2) Date: Dec. 18, 2023

(87) PCT Pub. No.: WO2023/138191
PCT Pub. Date: Jul. 27, 2023

(65) Prior Publication Data
US 2024/0269072 A1 Aug. 15, 2024

(30) Foreign Application Priority Data
Jan. 18, 2022 (CN) .......................... 202210055628.6

(51) Int. Cl.
| | |
|---|---|
| A61K 9/107 | (2006.01) |
| A61K 33/16 | (2006.01) |
| A61K 47/34 | (2017.01) |
| A61K 47/64 | (2017.01) |
| A61P 1/02 | (2006.01) |
| A61P 31/04 | (2006.01) |

(52) U.S. Cl.
CPC ............ *A61K 9/1075* (2013.01); *A61K 33/16* (2013.01); *A61K 47/34* (2013.01); *A61K 47/64* (2017.08); *A61P 1/02* (2018.01); *A61P 31/04* (2018.01)

(58) Field of Classification Search
CPC ...... A61K 9/1075; A61K 47/64; A61K 47/34; A61K 33/16; A61P 1/02; A61P 31/04
See application file for complete search history.

(56) References Cited

U.S. PATENT DOCUMENTS
2021/0330599 A1  10/2021  Benoit et al.

FOREIGN PATENT DOCUMENTS
| | | |
|---|---|---|
| CN | 104093768 | 10/2014 |
| CN | 107353334 | 11/2017 |
| CN | 107446095 | 12/2017 |
| CN | 114533669 | 5/2022 |
| WO | 2015155753 | 10/2015 |
| WO | 2020211859 | 10/2020 |

OTHER PUBLICATIONS

Honda et al., Biomacromolecules, 2020, 21, 9, p. 3826-3835 (Year: 2020).*
Yue Xu et al., "Dental plaque-inspired versatile nanosystem for caries prevention and tooth restoration", Bioactive Materials, Jun. 21, 2022, pp. 418-433, vol. 20.
"International Search Report (Form PCT/ISA/210) of PCT/CN2022/131838", mailed on Jan. 12, 2023, with English translation thereof, pp. 1-6.
"Written Opinion of the International Searching Authority (Form PCT/ISA/237) of PCT/CN2022/131838", mailed on Jan. 16, 2023, pp. 1-5.

* cited by examiner

*Primary Examiner* — Michael G. Hartley
*Assistant Examiner* — Leah H Schlientz
(74) *Attorney, Agent, or Firm* — JCIP GLOBAL INC.

(57) ABSTRACT

The present disclosure provides an oral care composition and a preparation method, and an application thereof. The composition includes: a drug-loaded micelle, wherein the drug-loaded micelle includes a polymer micelle and an enamel restoration drug physically wrapped in the polymer micelle, and the polymer micelle is micelle particles formed by a water-soluble polymer with a structure shown by Formula I in an aqueous solution with presence of tannic acid and the micelle particles have a shell connected to a salivary protein polypeptide through chemical bonds. The oral care composition in the present disclosure enables the salivary protein polypeptide to adhere to the surfaces of teeth so as to open the borate ester bond between the tannic acid and the water-soluble polymer in an acidic environment generated by the dental caries and release the tannic acid and sodium fluoride, thus achieving the purpose of preventing dental caries and restoring tooth defects.

9 Claims, 6 Drawing Sheets

ORAL CARE COMPOSITION, AND PREPARATION METHOD AND APPLICATION THEREOF

CROSS-REFERENCE TO RELATED APPLICATION

This application is a 371 of international application of PCT application serial no. PCT/CN2022/131838, filed on Nov. 15, 2022, which claims the priority benefit of China application no. 202210055628.6, filed on Jan. 18, 2022. The entirety of each of the above-mentioned patent application is hereby incorporated by reference herein and made a part of this specification.

BACKGROUND OF THE INVENTION

1. Technical Field

The present disclosure relates to the field of biological materials and the oral care technologies, and in particular to an oral care composition, and a preparation method and an application thereof.

2. Background Art

Dental caries is one of the major common diseases and high-incidence diseases in the current dental care, which subsequently leads to dental defects which may further result in complete loss of the dental morphology, and thus affecting the occlusal function. When a plurality of teeth are defected and even the occlusal function is lost, the oral function and aesthetics of the patients will be severely harmed. In the current major treatment approaches, after the infected tissues are removed mechanically and/or chemically, the defected tissues are reconstructed and repaired with restorative materials to achieve the purpose of restoring the tooth morphologies and functions. However, seen from the entire development process of the dental defect diseases, it is a remedial measure after the damage formation. Further, after the dental defect restoration, the risk of secondary caries is still present. Therefore, it is necessary to develop a method of preventing and restoring an early dental defect from the cause of diseases, which will bring great social benefits and application prospect.

Current studies show that bacterial infection is the major cause of dental caries. The major pathogenic bacterium *Streptococcus mutans* (*S. mutans*) aggregates and colonizes on the dental surface, then produces acid and demineralizes the dental hard tissues and finally results in loss of the dental hard tissues. At present, the medication methods for the dental caries mostly involve using primer or mouth wash or doping an antibacterial drug into a filling material to improve the antibacterial performance of the restorative interface. However, these methods still have the disadvantages of no sustained release of drug, and no strong specificity and the like. It is of great clinical significance to identify the dental caries at an early stage and perform intervention to interrupt its further development while restoring defected tissues.

SUMMARY OF THE INVENTION

For the disadvantages of short residence time in oral cavity, no sustained release of drug and no strong specificity for the existing oral care products, the present disclosure provides an oral care composition capable of adhering to dental surfaces, realizing sustained release of drug and quick release of drug in an acidic environment created by the dental caries, and a preparation method and an application thereof.

The technical scheme of the present disclosure is described below.

On one hand, the present disclosure provides an oral care composition, including a drug-loaded micelle, wherein the drug-loaded micelle includes a polymer micelle and an enamel restoration drug physically wrapped in the polymer micelle, and the polymer micelle with a structure shown in Formula I is a micelle particle formed by a water-soluble polymer in an aqueous solution with presence of tannic acid, and a shell of the micelle particle is connected to a salivary protein polypeptide through chemical bonds:

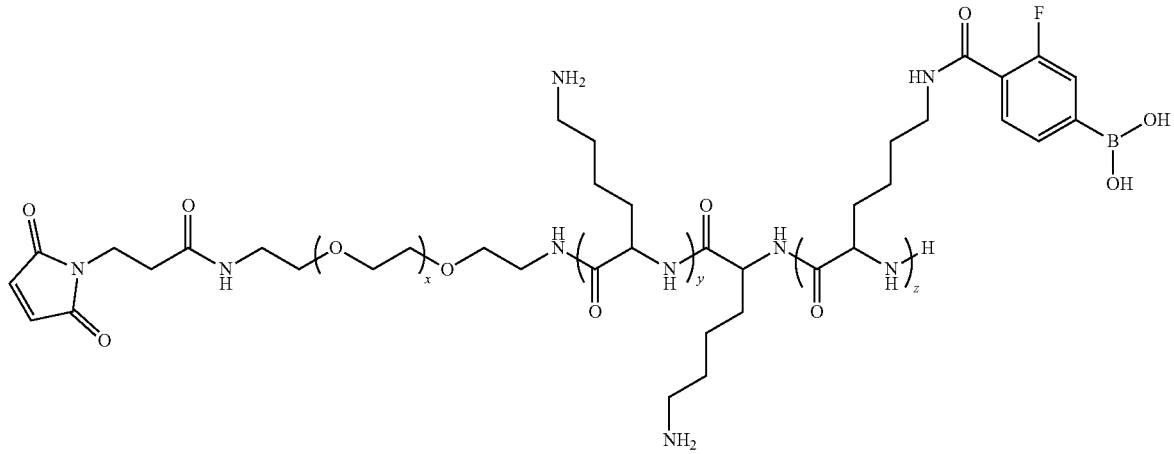

wherein, x, y, z are natural numbers which represent a degree of polymerization; and the weight-average molecular weight (Mw) of the water-soluble polymer is 5000 to 6000 g/mol; preferably, x=80 to 100, y=2 to 10, z=2 to 8; the number-average molecular weight (Mn) and the weight-average molecular weight (Mw) of the water-soluble polymer MAL-PEG-b-PLL/PBA with the structure shown in Formula I are 4400±100 g/mol and 5500±100 g/mol, respectively.

Based on the above technical scheme, the oral care composition provided by the present disclosure forms micelle particles through the water-soluble polymer in the aqueous solution with presence of tannic acid, and the enamel restoration drug is wrapped in the micelle particles. The salivary protein polypeptide stathelin connected with the surfaces of the micelle particles enable the drug-loaded micelle particles to adhere to dental enamel surfaces to achieve the purpose of long-time residence in the oral cavity. During the early stage of dental caries, the oral environment acidifies and the borate ester bond between the water-soluble polymer and the tannic acid breaks off; the chemically-gated channel is opened to release tannic acid and sodium fluoride to arrive at the effect of efficient bacteria resistance, promote re-mineralization restoration and to achieve smart and on-demand release of the drug, thereby realizing the purpose of preventing the dental caries and early restoration.

As a preferred example of the above technical scheme, the particle size of the micelle particles is 200 to 400 nm, further preferably, 300±50 nm to help the micelle particles to better seep into a biological membrane formed by *Streptococcus mutans*.

As a preferred example of the above technical scheme, the polymer micelle is connected to the salivary protein polypeptide through thioether bonds.

As a preferred example of the above technical scheme, the enamel restoration drug is sodium fluoride.

As a preferred example of the above technical scheme, the oral care composition is in the form of solid, paste, gel composition or liquid composition.

The above oral care composition further includes an anti-caries agent, a desensitizer, a viscosity modifier, a diluter, a surfactant, an emulsifier, a foam modifier, a pH regulator, an abrasive, a taste enhancer, a sweetener, a flavoring agent, a coloring agent, a preservative, amino acid, an antioxidant, an anti-dental calculus agent, a fluorion source, and a thickener as well as an active agent, a bonding agent and a whitener and a combination thereof used to prevent or treat the symptoms or diseases of the oral hard or soft tissues.

According a second aspect, the present disclosure provides a use of the above oral care composition in preparation of a drug used to reduce or inhibit the bacteria in the oral cavity of the patients and a use in preparation of a drug used to promote enamel re-mineralization restoration.

According to a third aspect, the present disclosure provides an in-vitro method of reducing or inhibiting bacteria or promoting enamel re-mineralization restoration in a removable oral apparatus of a patient, which includes applying the above oral care composition to a surface of the removable oral apparatus.

According to a fourth aspect, the present disclosure provides a method of preparing the above oral care composition, which includes:
  preparing the water-soluble polymer with a structure shown in Formula I;
  enabling the water-soluble polymer with a structure shown in Formula I to mix with an enamel restoration drug in an aqueous solution, and adding tannic acid dropwise to obtain a drug-loaded micelle dispersed in the aqueous solution;
  enabling the drug-loaded micelle and salivary protein polypeptide to generate a chemical bond in triethanolamine obtain the above oral care composition, where Preferably, the chemical bond is a thioether bond.

As a preferred example of the above technical scheme, a method of preparing the water-soluble polymer with the structure shown in Formula I includes:
  enabling 3-maleimidopropionic acid to be connected to one end of polyoxyethylene bis-amine through an amido bond to obtain MAL-PEG-NH$_2$;
  enabling MAL-PEG-NH$_2$ and ε-(benzyloxycarbonyl)-L-lysine N-carboxyanhydride to perform polymerization reaction to obtain MAL-PEG-b-PZLL;
  enabling MAL-PEG-b-PZLL to be subjected to debenzylation protection and then to perform amidation reaction with 3-fluoro-4-carboxy-phenylboronic acid to obtain the water-soluble polymer with the structure shown in Formula I.

In the present disclosure, the water-soluble polymer containing boric acid group is firstly prepared to form borate ester bond with tannic acid and conjugated with tannic acid to form micelle; during the process of forming micelle particles, sodium fluoride is physically wrapped; finally, the salivary protein polypeptide having the function of adhering to tooth is modified on the surface of the drug-loaded micelle particles to form a classical spherical micelle particles. The micelle particles can slowly release tannic acid and sodium fluoride under normal physiological conditions of the oral cavity so as to play the effect of antisepsis and restoration. When the dental caries occurs and the pH microenvironment in the oral cavity acidifies, tannic acid is released for breakage of the borate ester bond. Thus, tannic acid and sodium fluoride can be abruptly released at the early stage and slowly released for long later.

The present disclosure has the following advantages:
  The oral care composition prepared by the present disclosure has tooth adhesion and pH response such that it can identify *Streptococcus mutans* at an early stage so as to improve the bacteria targeting of the drug and local drug concentration, thus realizing smart and on-demand release. Hence, the toxic and side effects of the drug and the generation of the drug tolerance of the bacteria can be reduced, and further, the dental hard tissue defects can be prevented, bringing great advantages and potential.

DETAILED DESCRIPTION OF THE EMBODIMENTS

Figure 1:
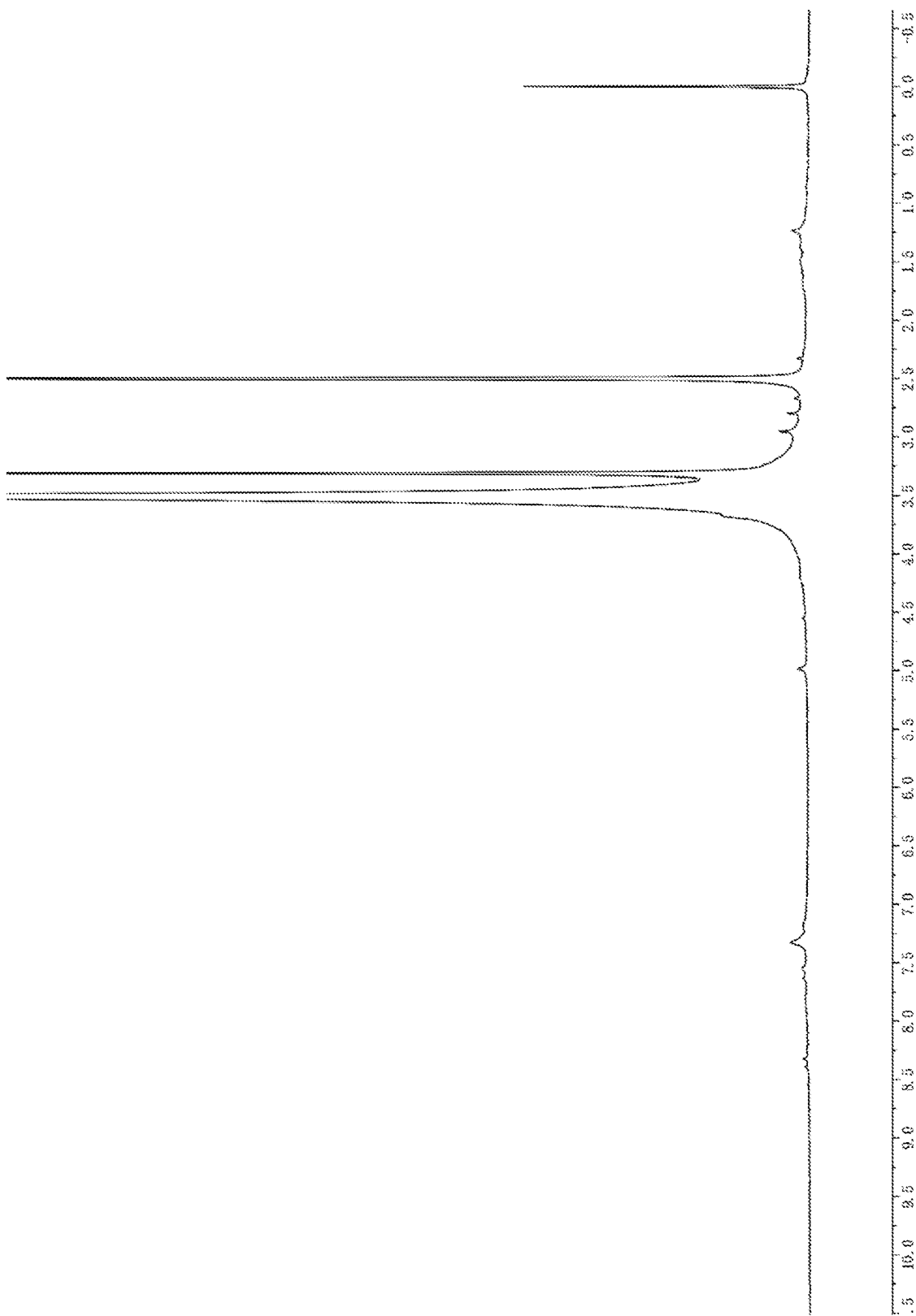
FIG. 1 is an NMR spectrogram of the water-soluble polymer MAL-PEG-b-PLL/PBA with the structure shown in Formula I, which is prepared in the present disclosure.

In order to make the object, the technical schemes and the beneficial effects of the present disclosure clearer and more intelligible, the present disclosure will be further set forth in details below in combination with specific examples. It should be understood that the specific examples described herein are merely illustrative and explanatory rather than limiting of the present disclosure.

The below are specific experiment examples of the present disclosure which are only preferred examples of the present disclosure and not used to limit the specific schemes of the present disclosure. The selection and means for some materials are optional for those skilled in the arts but the alternative schemes entirely covering the principle all fall within the scope of protection of the present disclosure.

Especially, in the examples of the present disclosure, the selected raw materials are commercially available.

Example 1: Preparation of a Micelle Composite Material Loading Tannic Acid and Sodium Fluoride and Connecting a Salivary Protein Polypeptide (1) Preparation of a Water-Soluble Polymer Polyoxyethylene bis-amine (CAS No.: 24991-53-5, $NH_2C_2H_2$—$(CH_2O)_n$—$C_2H_2NH_2$) was co-reacted with 3-maleimidopropionic acid (MAL-) to modify MAL on the polymer so as to obtain a product MAL-PEG-$NH_2$.

ε-(benzyloxycarbonyl)-L-lysine N-carboxyanhydride (Lys(Z)-NCA) (1.96 g, 6.4 mmol) was dissolved in 30 ml of N,N-dimethylformamide (DMF), and then MAL-PEG-$NH_2$ (2.0 g, 0.4 mmol) was added, and then stirred for 72 h under the dry argon of 35° C. to enable them to perform polymerization reaction. Then, rotary evaporation was performed on the solvent and a product was dissolved in 25 mL $CHCl_3$ and then placed in excess diethyl ether for precipitation to obtain a product MAL-PEG-b-PZLL.

In order to remove the benzyl protective group and remove the protection for amino so as to subsequently enable the hydrogen atoms on the amino to be substituted by acylamino, amidation reaction was performed: 2.0 g of MAL-PEG-b-PZLL was dissolved in 20 mL $CF_3COOH$ and then HBr was added (33 wt. % dissolved in HOAc, 2 ml). The mixture was stirred for 2 h at the temperature of 0° C. and then placed in cold diethyl ether for precipitation. This precipitate was dissolved in the DMF and then precipitated again in the excess diethyl ether to remove residual $CF_3COOH$ to obtain a product MAL-PEG-b-PLL which was dried under vacuum at room temperature.

MAL-PEG-b-PLL (100 mg, 0.18 mmol) was dissolved in 10 ml of sodium bicarbonate solution (50 mM, pH 8.5) containing D-mannitol (100 mg, 0.55 mmol), and then 1.7 ml of 3-fluoro-4-carboxy-phyenylboronic acid (FPBA) solution dissolved in methyl alcohol was added and then a couplant 4-(4,6-dimethoxy-1,3,5-triazin-2-yl)-4-methyl-morpholinium chloride n-hydrate (DMT-MM) (254 mg, 0.92 mmol) was added, and then the reaction mixture was stirred for 12 h at the temperature of 25° C. to enable them to perform amidation reaction so as to connect FPBA with MAL-PEG-b-PLL. With 0.01 N NaOH solution, 0.01N HCl solution and de-ionized water, the reaction solution was dialyzed using a dialysis bag (MWCO 3500) and a dialysis product was frozen and dried to obtain a product MAL-PEG-b-PLL/PBA, namely, the water-soluble polymer with the structure shown in Formula I:

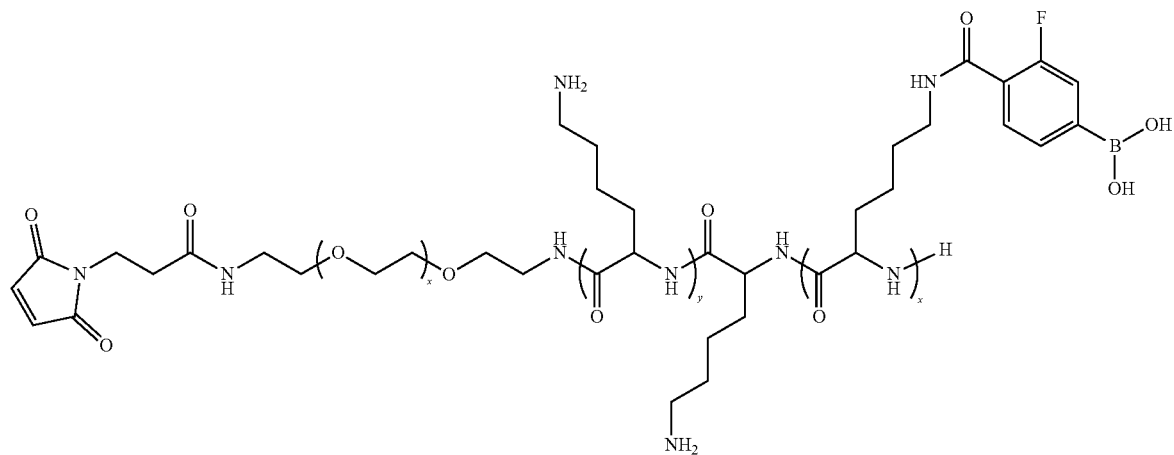

Formula I wherein, x, y, and z are natural numbers which represent a degree of polymerization. The number-average molecular weight (Mn) and the weight-average molecular weight (Mw) of MAL-PEG-b-PLL/PBA were measured as 4458 g/mol and 5642 g/mol, respectively.

MAL-PEG-b-PLL/PBA obtained by the above method was subjected to NMR to obtain a spectrogram as shown in FIG. 1. It can be known from FIG. 1 that the peak at about 7.3 ppm is a characteristic peak of FPBA phenylene, which proves that FPBA is successfully connected to the polymer through conjugation with amido. The transmission electron microscope result of MAL-PEG-b-PLL/PBA is as shown in a, d and g of FIG. 2. In the drawings, it can be seen that a huge number of scattered particles with smaller particle size are around the polymer with larger particle size. Based on the scale in the drawing, it can be known that the larger polymer particle size is only about 100 nm and the micelle structure is not formed.

(2) Loading of sodium fluoride: 5 mg of MAL-PEG-b-PLL/PBA was dissolved in 4 ml of de-ionized water to obtain a carrier aqueous solution; meanwhile, 548 µL of sodium fluoride aqueous solution (5 mg/mL) was added dropwise to the carrier aqueous solution and then stirred to full dissolution so as to obtain a sodium fluoride-carrier aqueous solution.

(3) Synthesis of micelle particles: a 5 mg/mL tannic acid aqueous solution was prepared, and 274 µL of tannic acid aqueous solution was taken and then slowly added dropwise at a constant speed to the sodium fluoride-carrier aqueous solution, and then stirred at room temperature to obtain a solution which was collected through ultrafiltration centrifugation for 20 minutes to obtain a drug-loaded micelle particles (CLM@NaF) loading sodium fluoride and tannic acid. The transmission electron microscope image of CLM@NaF is as shown in b, e and h of FIG. 2.

(4) Polypeptide connection: 1 mg of salivary protein polypeptide DpSpSEEKC (Pep) and the drug-loaded micelle particles (CLM@NaF) were dispersed in pure triethanolamine (TEA) (pH-8.0), and then stirred for 2 h forcefully at room temperature and collected through ultrafiltration centrifugation for 20 minutes to obtain a polypeptide drug-loaded micelle particles (CLM@NaF-Pep) loading sodium fluoride and tannic acid and connecting salivary protein polypeptide. The transmission electron microscope image of CLM@NaF-Pep is as shown in c, f and i of FIG. 2.

Figure 2:
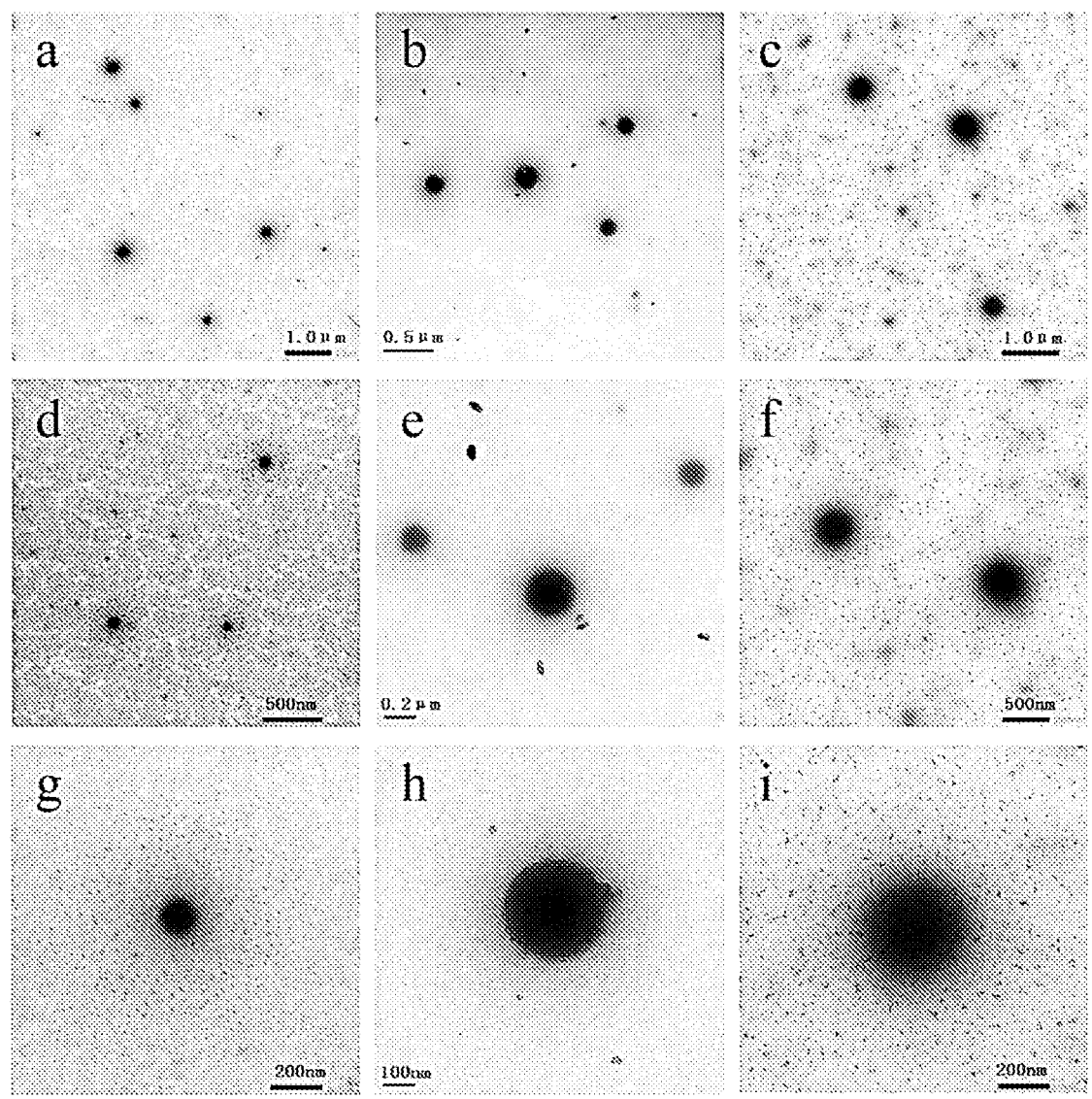
FIG. 2 is a transmission electron microscopy image of MAL-PEG-b-PLL/PBA, CLM@NaF and CLM@NaF-Pep prepared in the present disclosure.

It can be known from the b, e, h of FIG. 2, and the c, f and i of FIG. 2 that the particle size of the synthesized micelle particles is about 300 nm, and the synthesized micelle particles shaped as classical spherical kernel-shell structure with regular morphology and good dispersion. The loading of sodium fluoride and tannic acid and the connection with the polypeptide do not have adverse effect on the morphology and dispersion of the micelle particles.

Preparation of the control sample CLM (MAL-PEG-b-PLL/PBA+TA): tannic acid aqueous solution was directly added dropwise to the polymer MAL-PEG-b-PLL/PBA aqueous solution, and stirred, mixed and self-assembled and then subjected to ultrafiltration purification to obtain CLM (MAL-PEG-b-PLL/PBA+TA) micelle particles which differ from CLM@NaF only in that, without adding the sodium fluoride aqueous solution, the micelle particle structure only loading TA was synthesized, where NaF was not loaded.

Figure 3:
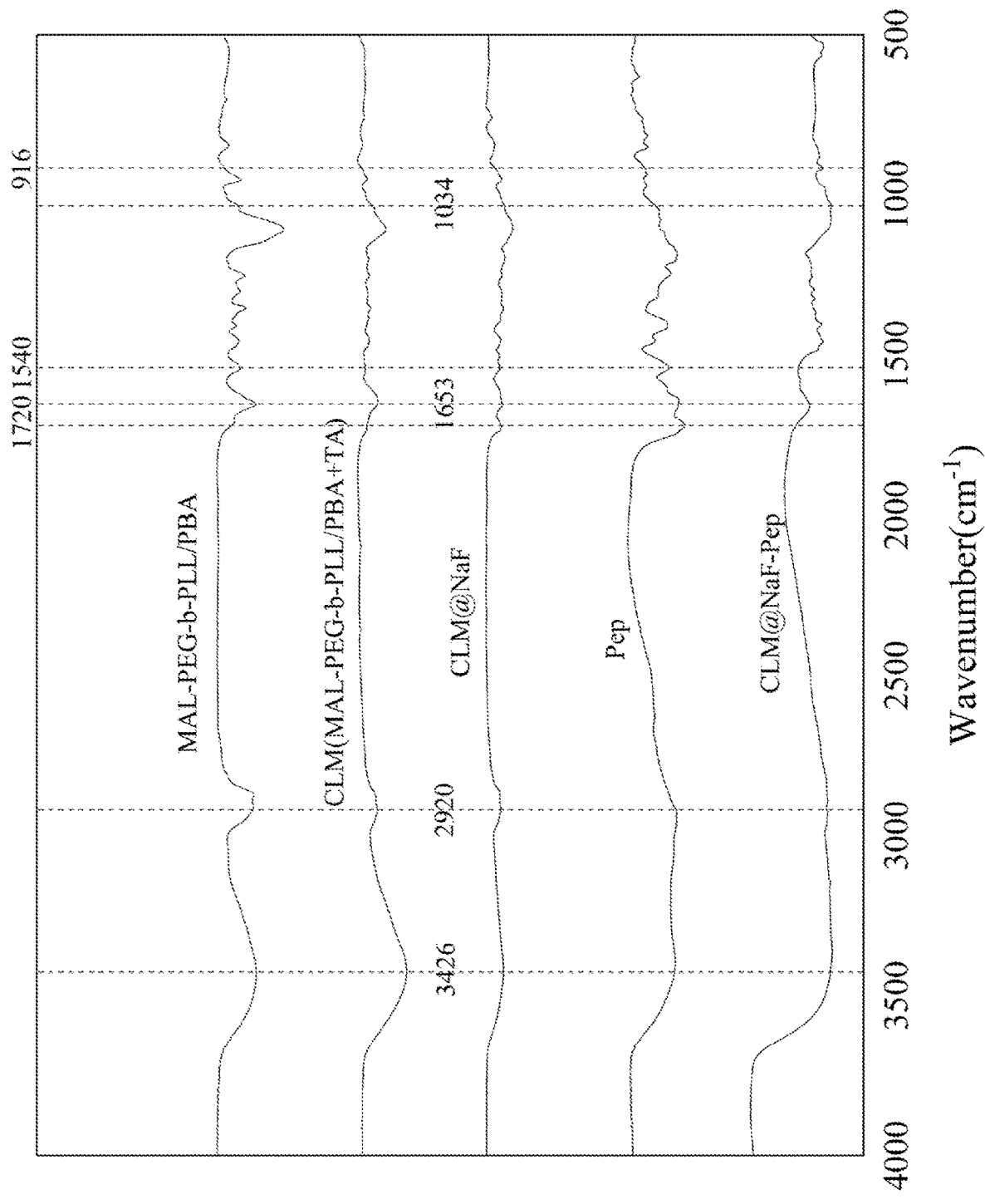
FIG. 3 shows an infrared spectrum detection result of MAL-PEG-b-PLL/PBA, CLM (MAL-PEG-b-PLL/PBA+ TA), CLM@NaF, Pep and CLM@NaF-Pep prepared in the present disclosure.

The infrared spectrum detection results of the water-soluble polymers MAL-PEG-b-PLL/PBA, CLM (MAL-PEG-b-PLL/PBA+TA), CLM@NaF. Pep and CLM@NaF-Pep prepared by the above method are as shown in FIG. 3. The results show that MAL-PEG-b-PLL/PBA, CLM (MAL-PEG-b-PLL/PBA+TA) and CLM@NaF have peak values at 1653 $cm^{-1}$, 1540 $cm^{-1}$ and 3426 $cm^{-1}$, respectively, which correspond to amide extension segments in the entire repeating and branching polymer structure: polypeptide (Pep) also has an amide peak at 1640 $cm^{-1}$ and 1540 $cm^{-1}$, respectively and has a small peak at 1720 $cm^{-1}$, which corresponds to sulfydryl of cysteine; the CLM@NaF-Pep sulfydryl belt disappears, and there are two new peaks at 1034 $cm^{-1}$ and 916 $cm^{-1}$, and these new extensions appear in the formation process of the thioether group engaging with the surface of CLM@NaF in Pep. Furthermore, the absorption of amide III is covered, which shows that the interaction with amino acid is substantially changed, and proves CLM@NaF and Pep are successfully connected through the thioether group.

Example 2: Test of pH Controlled Release of the Drug

The releases of drug in CLM@NaF-Pep under different pH conditions were detected by using a high performance liquid chromatograph and an ion exchange chromatograph. 2 ml of a newly-prepared CLM@NaF-Pep dispersion was transferred to a dialysis bag (MWCO 3500), and then soaked in 15 mL of 10 mM PBS with different pHs, and shaken at the temperature of 37° C. (with rotation of 100 r/min). 1 ml of dialyzate was collected at a fixed time interval (every 0.5 h, 1 h, 2 h, 4 h, 8 h, 12 h, 24 h) until 24 h. After one dialyzate collection was performed, a fresh buffer solution with equal volume was added to keep the total volume of the dialyzate unchanged. The contents of tannic acid and sodium fluoride in the dialyzate were detected by using the high performance liquid chromatograph and the ion exchange chromatograph. All tests were provided with three parallel control groups and their average values were calculated for comparison. The tests were repeated three times.

Figure 4:
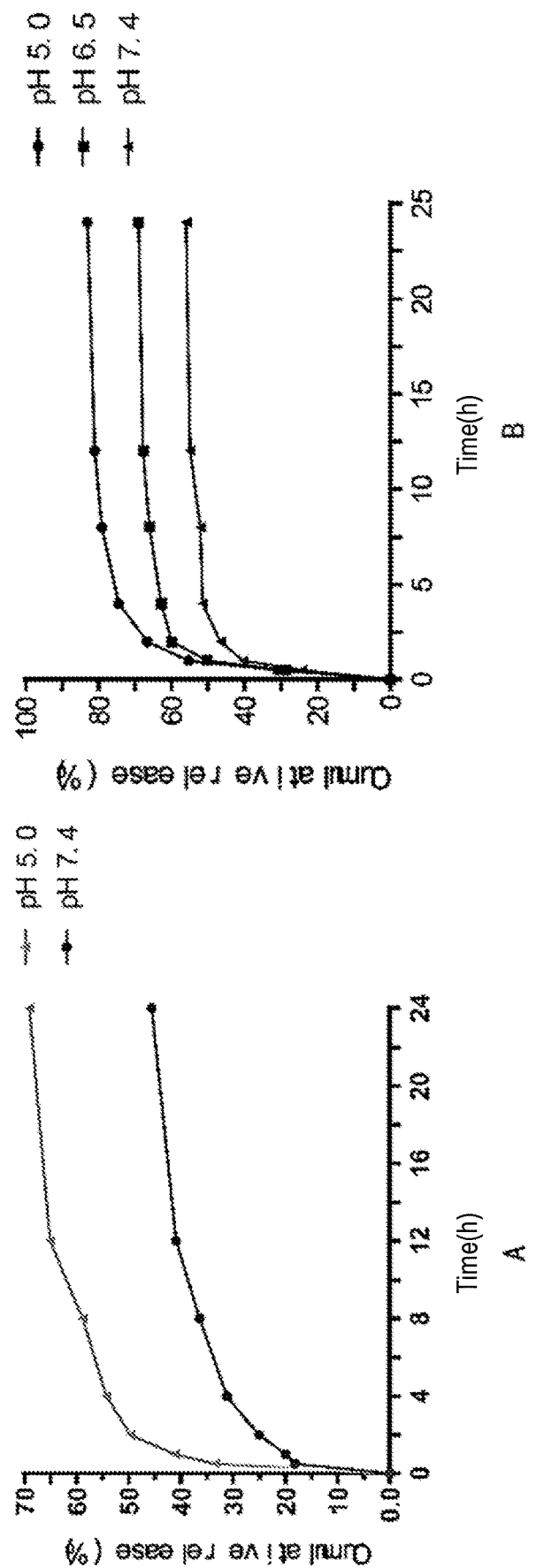
FIG. 4 shows a pH-controlled release effect of CLM@NaF-Pep prepared in the present disclosure on tannic acid and sodium fluoride.

The pH controlled release effect of CLM@NaF-Pep on tannic acid and sodium fluoride is as shown in FIG. 4: when the pH is 7.4 and 5.0, respectively, the controlled release effect of tannic acid is as shown in A of FIG. 4; when the pH is 7.4, 6.5 and 5.0, the controlled release effect of the sodium fluoride is as shown in B of FIG. 4. It can be known from FIG. 4 that, under normal physiological conditions (pH 7.4), the cumulative release rate of tannic acid and sodium fluoride within 24 hours are 40% and 50%, respectively, showing long-time sustained release effect and reflecting high stability of CLM@NaF-Pep. When the dental caries occurs and the microenvironment in the oral cavity acidifies (pH 5.0), tannic acid is released for breakage of the borate ester bond. Thus, tannic acid can be abruptly released at the early stage and slowly released for long later with the cumulative release rate within 24 hours close to 70%, and sodium fluoride wrapped therein is also quickly released along with pH acidification and micelle cracking, with the cumulative release rate within 24 hours being about 80%.

Example 3: Test of Effect of Inhibiting Growth of *Streptococcus mutans*

*Streptococcus mutans* cultured to the exponential phase was collected through centrifugation of 3 min (5000 rpm) and diluted to 106 CFU/mL by using BHI medium to obtain a bacteria suspension.

To the BHI mediums with the pHs being 7.4, 6.5, and 5.0, respectively was added CLM@NaF-Pep to prepare an experimental group dispersion; with PBS as blank control group solution and chlorhexidine (CHX) as positive control group solution, they were filled into 96-well plate (each well is 160 µL). Next. 40 µL of the above bacteria suspension was added to the experimental group dispersion and the control group solution and uniformly mixed. The 96-well plate was placed into 37° C. incubator and held for 0.5, 1, 2, 4, 8, 12 and 24 h and then 100 µL of culture solution was taken from each group and inoculated into a new 96-well plate. By using a microplate reader, the absorbance of each well was recorded at 600 nm to evaluate its antibacterial activity. All experiments were provided with three repeating holes to calculate their average values for comparison. The experiment was repeated three times.

Figure 5:
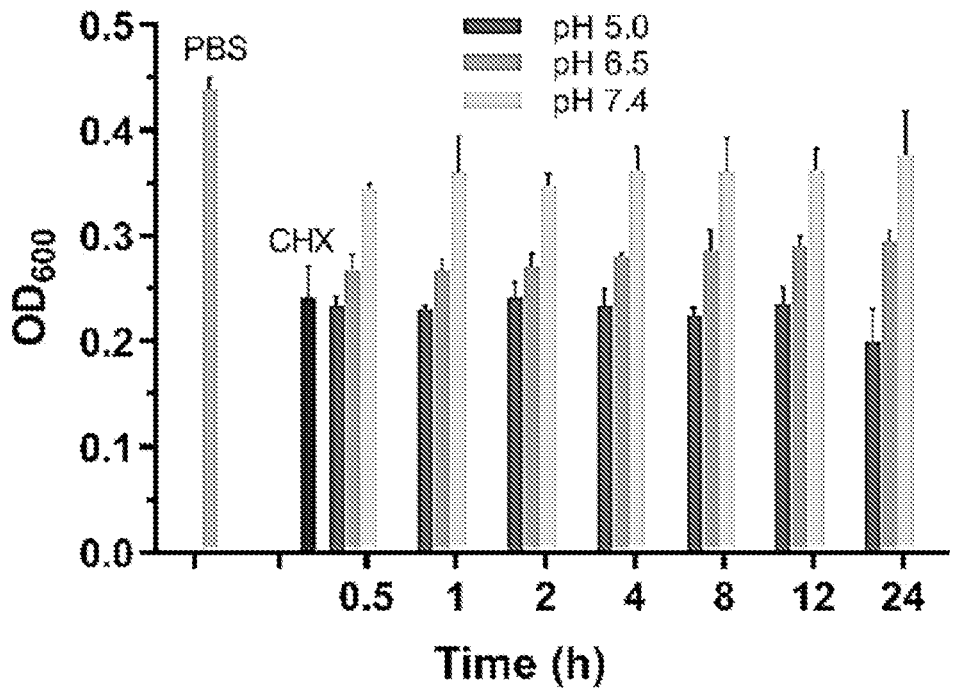
FIG. 5 is a growth curve of the inhibition, on *Streptococcus mutans*, of CLM@NaF-Pep prepared in the present disclosure as a nano-material for preventing the dental caries and performing restoration at an early stage.

As shown in FIG. 5, it is a growth curve of inhibiting *Streptococcus mutans*. It can be known from FIG. 5 that CLM@NaF-Pep exhibits efficient antibacterial activity for *Streptococcus mutans*, and along with decrease of pH, its activity for inhibiting the growth of *Streptococcus mutans* increases. When *Streptococcus mutans* is at the pH of 5.0, the sterilizing effect is even higher than chlorhexidine.

Example 4: Detection of the Activity Against Cariogenic Biological Membrane

An amount of hydroxyapatite (HA) sheets (with diameter of 5 mm and thickness of 2 mm) was prepared, and sterilized by autoclaving method. The HA sheets were treated by using an equal amount of de-ionized water ($ddH_2O$), CLM@NaF aqueous dispersion, Pep aqueous solution and CLM@NaF-Pep aqueous dispersion, and washed three times with PBS to remove the substances not clinging to the HA sheets so as to obtain four groups of pre-treated HA sheets. The *Streptococcus mutans* grown to the exponential phase was diluted using the BHI medium to $OD_{600}$ which is 0.5; then, the bacterial suspension was inoculated to the pre-treated HA sheets and placed in a 48-well plate such that the pre-treated HA sheets were completely immersed in the *Streptococcus mutans* suspension and then subjected to anaerobic culture for 1.5 h at the temperature of 37° C. Subsequently, the bacterial solution was sucked out and the non-clinging bacterial solution was removed carefully with PBS and then an appropriate amount of sugar-containing medium was added to perform anaerobic culture for 24-48 h at the temperature of 37° C. Finally, the samples were washed with the PBS and the biological membranes on the HA sheets were collected ultrasonically and the biological membrane suspension was continuously diluted and spread on the BHI agar plate for culture of 48 h, and then the number of the bacterial colonies was calculated. The experiment was repeated three times. The colony forming units (CFU) against the biological membrane of the *Streptococcus mutans* were counted as shown in FIG. 6.

Figure 6:
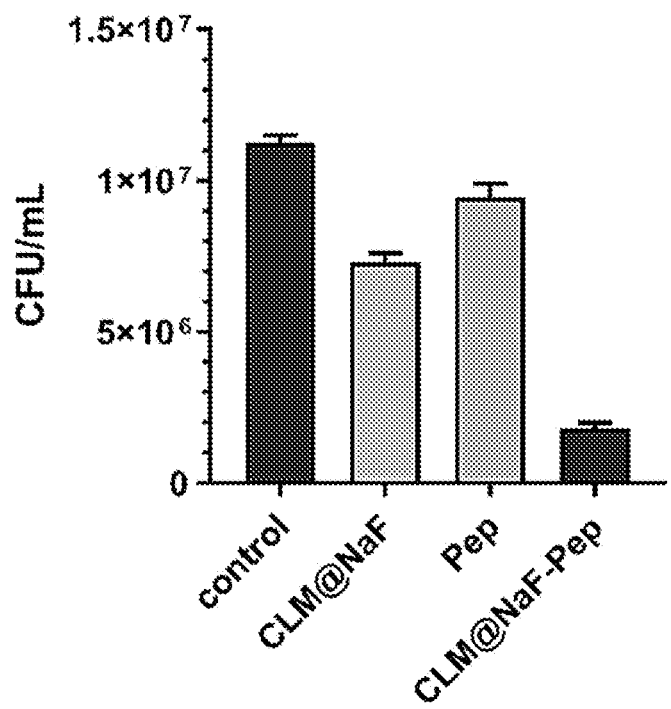
FIG. 6 is an effect diagram showing capabilities against the biological membrane of the *Streptococcus mutans*, of CLM@NaF-Pep prepared in the present disclosure and the control group.

The result of FIG. 6 shows that compared with the HA sheets treated only with the de-ionized water (represented by control in FIG. 6), the HA sheets treated only with the polypeptide aqueous solution (represented by Pep in FIG. 6) have no obvious antibacterial and anti-biological membrane activity and the HA sheets treated only with CLM@NaF aqueous dispersion (represented by CLM@NaF in FIG. 6) have a degree of antibacterial activity but cannot reside in the oral cavity due to the buffer effect of the saliva and thus has a weak anti-biological membrane capability; the HA sheets treated with CLM@NaF-Pep aqueous dispersion (represented by CLM@NaF-Pep in FIG. 6) not only have antibacterial adhesion but also seep into the biological membrane and kill the bacteria in the biological membrane, which proves that the constructed CLM@NaF-Pep has high removal effect on the cariogenic biological membrane on the surfaces of teeth.

Example 5: Detection on Inhibiting Enamel Demineralization and Promoting its Re-Mineralization A third molar of a person without dental caries was collected and its root was sawed off slowly. From the mesial and distal direction, perpendicular to the major axis of the tooth, the dental crown was cut into a lip portion and a tongue portion, and the samples were cut into $5*4*1.5$ mm$^3$ dental enamel sheets. The dental enamel sheets were polished suing 600-mesh and 1200-mesh abrasive papers and then ultrasonicated for 20 min in the de-ionized water ($ddH_2O$). The enamel surface of the tooth was acid-etched for 1 min by using 37% phosphoric acid, and then washed for 1 min by using $ddH_2O$. The dental sheets were randomly divided into four groups (blank control group, CLM@NaF group, Pep group, and CLM@NaF-Pep group), and respectively immersed in the de-ionized water, the CLM@NaF aqueous dispersion, the Pep aqueous solution and CLM@NaF-Pep aqueous dispersion, and then the non-clinging substances were removed using PBS. The enamel surfaces of each group of dental sheets were placed facing upward and other surfaces were covered with an acid-resistant nail polish. Then, the dental sheets were cultured for 5 h in 7 ml of demineralization solution (2.2 mM $CaCl_2$), 2.2 mM$NaH_2PO_4$, 0.05 M acetic acid, pH 4.5) at the temperature of 37° C., and cultured for 24 h in 7 ml of re-mineralization solution (2.58 mM $CaCl_2 \cdot 2H_2O$, 1.55 mM $KH_2PO_4$, 1 mg/L NaF, 180 mMNaCl, 50 mM Tris-HCl, pH 7.6) at the temperature of 37° C. The Ca and P concentrations before and after wetting were detected by using a plasma spectrometer. The enamel exposure area was calculated, and the Ca/P loss amount was denoted by $\mu g/mm^2$. Further. The morphologies of the enamel surface and the cross sectional surface were qualitatively analyzed by using a scanning electron microscope, with a result shown in FIG. 7.

Figure 7:
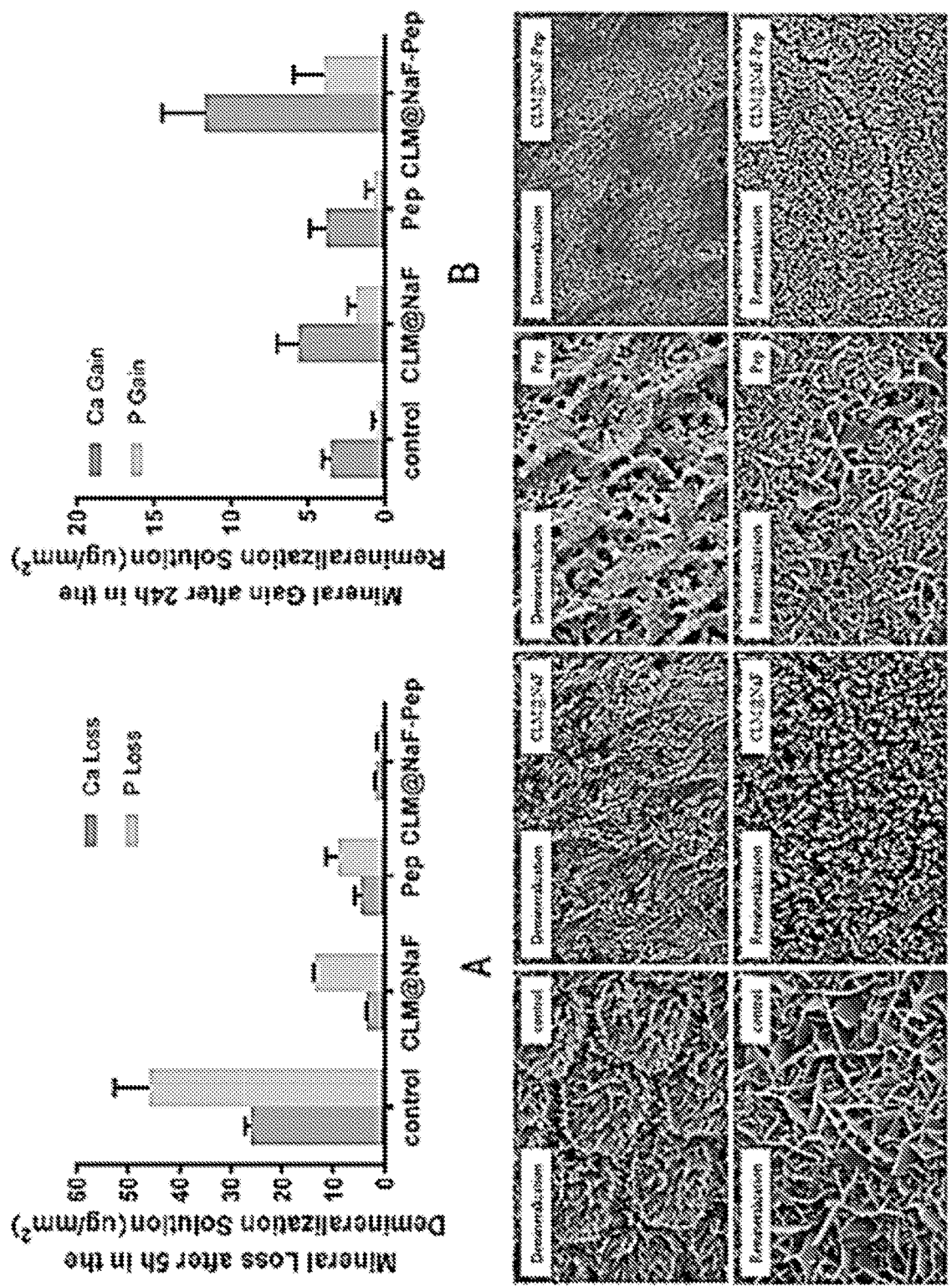
FIG. 7 is a quantitative detection and scanning electron microscope image of calcium and phosphorus ions for inhibiting enamel demineralization and promoting its remineralization in CLM@NaF-Pep prepared in the present disclosure and each control group.

It can be known from FIG. 7 that, in the demineralization solution, after the dental enamel is treated by using the micelle particles connected with the polypeptide, the loss amount of the calcium and phosphorus ions is significantly lower than the blank control group (represented by control in FIG. 7), the Pep group (represented by Pep in FIG. 7) and the CLM@NaF group (represented by CLM@NaF in FIG. 7) (A of FIG. 7); similarly, in the re-mineralization environment, the CLM@NaF-Pep group (represented by CLM@NaF-Pep in FIG. 7) also shows more significant increase effect of the calcium and phosphorus ions (B of FIG. 7). By using the scanning electron microscope image (C of FIG. 7), it can be found that in the demineralization solution, the enamel rods, the structure between enamel rods and enamel rod sheaths are all dissolved in the blank control group, and the enamel rod structures in the Pep group and CLM@NaF group are also destroyed to different degrees, but the enamel surfaces in the CLM@NaF-Pep group are still relatively smooth; in the re-mineralization environment, the de-mineralized enamel surface in the CLM@NaF-Pep group has a large amount of new oriented and orderly-grown hydroxyapatite crystals. It proves that the constructed CLM@NaF-Pep has significant effect of inhibiting dental enamel demineralization and promoting its re-mineralization.

The above examples are used only to illustrate the present disclosure rather than limit the present disclosure. Although the present disclosure is detailed with reference to the preferred examples, persons of ordinary skills in the arts should understood that changes or equivalent replacements can be made to the technical schemes of the present disclosure without departing from the spirit and scope of the technical schemes of the present disclosure.

What is claimed is:

1. An oral care composition, comprising a drug-loaded micelle, wherein the drug-loaded micelle comprises a polymer micelle and an enamel restoration drug physically wrapped in the polymer micelle, and the polymer micelle is a micelle particle formed by a water soluble polymer with a structure shown in Formula I in an aqueous solution with presence of tannic acid, and a shell of the micelle particle is connected to a salivary protein polypeptide through chemical bonds:

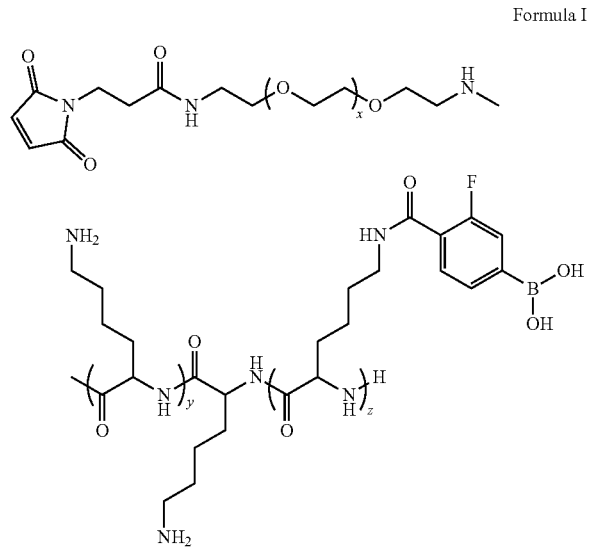

Formula I wherein, x=80 to 100, y=2 to 10, and z-2 to 8; and a weight-average molecular weight (Mw) of the water-soluble polymer is 5000 to 6000 g/mol.

2. The oral care composition of claim 1, wherein a particle size of the micelle particles is 200 to 400 nm.

3. The oral care composition of claim 1, wherein the enamel restoration drug is sodium fluoride.

4. The oral care composition of claim 1, wherein the oral care composition is in a form of solid, paste, gel composition or liquid composition.

5. The oral care composition of claim 1, wherein the oral care composition further comprises an anti-caries agent, a desensitizer, a viscosity modifier, a diluter, a surfactant, an emulsifier, a foam modifier, a pH regulator, an abrasive, a taste enhancer, a sweetener, a flavoring agent, a coloring agent, a preservative, amino acid, an antioxidant, an anti-dental calculus agent, a fluorion source, a thickener, an active agent used to prevent or treat symptoms or diseases of oral hard or soft tissues, a bonding agent, a whitener, or a combination thereof.

6. An in-vitro method of reducing or inhibiting bacteria or promoting enamel re-mineralization restoration in a removable oral apparatus of a patient, comprising applying the oral care composition of claim 1 to a surface of the removable oral apparatus.

7. A method of preparing the oral care composition of claim 1, comprising:
preparing the water-soluble polymer with a structure shown in Formula I;
mixing the water-soluble polymer with the structure shown in Formula I with an enamel restoration drug in an aqueous solution, and adding tannic acid dropwise to obtain a drug-loaded micelle dispersed in the aqueous solution;
enabling the drug-loaded micelle and salivary protein polypeptide to generate a chemical bond in triethanolamine to obtain the oral care composition.

8. The method of claim 7, wherein preparing the water-soluble polymer with the structure shown in Formula I comprises:
enabling 3-maleimidopropionic acid to be connected to one end of polyoxyethylene bis-amine through an amido bond to obtain MAL-PEG-NH$_2$;
enabling the MAL-PEG-NH$_2$ and ε-(benzyloxycarbonyl)-L-lysine N-carboxyanhydride to perform polymerization reaction to obtain MAL-PEG-b-PZLL;
enabling the MAL-PEG-b-PZLL to be subjected to debenzylation protection and then to perform amidation reaction with 3-fluoro-4-carboxy-phyenylboronic acid to obtain the water-soluble polymer with the structure shown in Formula I.

9. The method of claim 8, wherein preparing the water-soluble polymer with the structure shown in Formula I comprises:
co-reacting the polyoxyethylene bis-amine with the 3-maleimidopropionic acid to modify MAL on the polymer so as to obtain a product MAL-PEG-NH$_2$;
dissolving the ε-(benzyloxycarbonyl)-L-lysine N-carboxyanhydride in N,N-dimethylformamide, and then performing a polymerization reaction by adding the MAL-PEG-NH$_2$, then dissolving a product from the polymerization reaction in CHCl$_3$, followed by placing in excess of diethyl ether for precipitation to obtain a product MAL-PEG-b-PZLL;
dissolving the MAL-PEG-b-PZLL in CF$_3$COOH, stirring after adding HBr, and then placing in cold diethyl ether for precipitation to obtain a product MAL-PEG-b-PLL, followed by dissolving in a sodium bicarbonate solution containing D-mannitol, and then adding 3-fluoro-4-carboxy-phyenylboronic acid solution dissolved in methyl alcohol followed by adding a couplant 4-(4,6-dimethoxy-1,3,5-triazin-2-yl)-4-methylmorpholinium chloride n-hydrate to enable an amidation reaction so as to connect FPBA with the MAL-PEG-b-PLL to obtain a product MAL-PEG-b-PLL/PBA.

* * * * *